United States Patent [19]

Barone, Jr.

[11] Patent Number: 4,934,382

[45] Date of Patent: Jun. 19, 1990

[54] PROTECTIVE SHEATH WITH MANIPULATION TABS

[76] Inventor: Richard J. Barone, Jr., 10-D Weaver St., Greenwich, Conn. 06831

[21] Appl. No.: 375,057

[22] Filed: Jul. 3, 1989

[51] Int. Cl.⁵ .................................... A61F 13/00
[52] U.S. Cl. .................................... 128/844; 128/856; 604/349
[58] Field of Search ............... 128/844, 849, 851, 856, 128/842; 604/346, 347, 349, 351

[56] References Cited

U.S. PATENT DOCUMENTS

| | | | |
|---|---|---|---|
| 3,018,484 | 1/1962 | Koehn | 128/844 X |
| 3,968,792 | 7/1976 | Small | 128/856 |
| 4,153,054 | 5/1979 | Boone | 128/856 |
| 4,308,864 | 1/1982 | Small et al. | 128/856 |
| 4,805,604 | 2/1989 | Spery | 128/79 |

FOREIGN PATENT DOCUMENTS

| | | | |
|---|---|---|---|
| 0111720 | of 1928 | Austria | 604/349 |
| 2410697 | 12/1974 | Netherlands | 604/349 |

Primary Examiner—Robert A. Hafer
Assistant Examiner—Lynda M. Cofsky
Attorney, Agent, or Firm—Samuelson & Jacob

[57] ABSTRACT

A protective sheath of the type supplied with a portion of the protective sheath in a rolled up configuration for application to a member by unrolling the rolled up portion along the member includes application tabs interleaved with the rolled up portion of the protective sheath and available for gripping to pull the application tabs and unroll the rolled up portion along the member and assist in the application of the protective sheath to the member. In some embodiments, the protective sheath includes removal tabs extending along the applied protective sheath and available for gripping to pull the removal tabs and roll up a portion of the protective sheath to assist in the removal of the protective sheath from the member.

10 Claims, 7 Drawing Sheets

PROTECTIVE SHEATH WITH MANIPULATION TABS

The present invention relates generally to protective sheaths and pertains, more specifically, to improvements which facilitate the application and, in some embodiments, the removal of protective sheaths, such as condoms, to and from generally complementary members.

A wide variety of items constructed in the form of a protective sheath of thin, flexible material currently is available for selective application to various members requiring protection. For example, sheaths of thin rubber, or other thin elastomeric materials, are applied to a physician's finger during certain examining procedures for maintaining aseptic contact; surgical gloves of like materials are applied to a surgeon's hands to maintain sterile conditions during surgical procedures; condoms of elastomeric materials, or other thin membrane-like materials, are applied to the male organ for prophylactic purposes; and liners of protective materials are applied to the inside surfaces of tubular conduits to protect against contamination or the effects of corrosive elements conveyed through the conduits.

One of the more ubiquitous of the above-enumerated items is the condom of the type which is packaged in a rolled up, generally flattened configuration and must be unrolled for application to a male organ. These condoms usually are coated with, or otherwise immersed in, one or more compounds providing a lubricant, a spermicide, or a bactericide, all of which render the condom difficult, or at least uncomfortable, to handle during application. In addition, removal may be difficult, or uncomfortable, and may require careful handling to maintain aseptic conditions, or at least a modicum of cleanliness.

The present invention is directed to an improvement which facilitates the application, and in some embodiments the removal, of protective sheaths of the type which are supplied in a rolled up configuration and are unrolled for application, and provides several objects and advantages, some of which may be summarized as follows: Simplifies application by facilitating the initial orientation and location of the rolled up protective sheath upon the corresponding member and then unrolling of the protective sheath for application to the member; Avoids direct handling of the protective sheath itself during application, and in some embodiments during removal, so as to maintain aseptic conditions, as well as general cleanliness, while facilitating the manipulations required for application and removal; Provides an ergonomic construction enabling ease of use with minimal instruction; Permits increased ease of use of the protective sheath without disturbing the function of the protective sheath, and with no deleterious effects upon the disposable nature of the protective sheath; Provides a simplified construction which is economical to manufacture in large quantities of uniform high quality.

The above objects and advantages, as well as further objects and advantages, are attained by the present invention which may be described briefly as an improvement in a protective sheath, such as a condom, having first and second ends and a tubular wall of relatively thin, rollable flexible material, the tubular wall including an outer surface and an inner surface and capable of being rolled and unrolled between a rolled up state, wherein at least a portion of the tubular wall is rolled up upon itself in a relatively flattened configuration, and an unrolled state, wherein the tubular wall portion extends axially in a tubular configuration, for application of the protective sheath along a generally complementary cylindrical surface having axially opposite ends by juxtaposing the tubular wall, in the rolled up state, with one of the opposite ends of the cylindrical surface and then unrolling the rolled up tubular wall portion to extend the tubular wall from the rolled up state toward the unrolled state along the cylindrical surface, the improvement comprising: at least one manipulation tab, either in the form of an application tab or in the form of a removal tab, interleaved with the rolled up portion of the tubular wall, when the tubular wall is in the rolled up state, and juxtaposed with the appropriate outer or inner surface of the tubular wall such that the manipulation tab extends along the corresponding outer or inner surface of the tubular wall from the first or second end of the protective sheath toward the opposite end thereof, the manipulation tab including a gripping portion extending beyond the tubular wall portion adjacent the corresponding end of the protective sheath so as to be available for gripping and pulling away from the first end of the protective sheath either to unroll the rolled up tubular wall portion toward the unrolled state of the tubular wall and apply the protective sheath along the cylindrical surface or to roll the tubular wall portion from the unrolled state of the tubular wall toward the rolled up state and effect removal of the protective sheath from the cylindrical surface.

The invention will be understood more fully, while still further objects and advantages thereof will become apparent, in the following detailed description of preferred embodiments of the invention illustrated in the accompanying drawing, in which.

Figure 1:
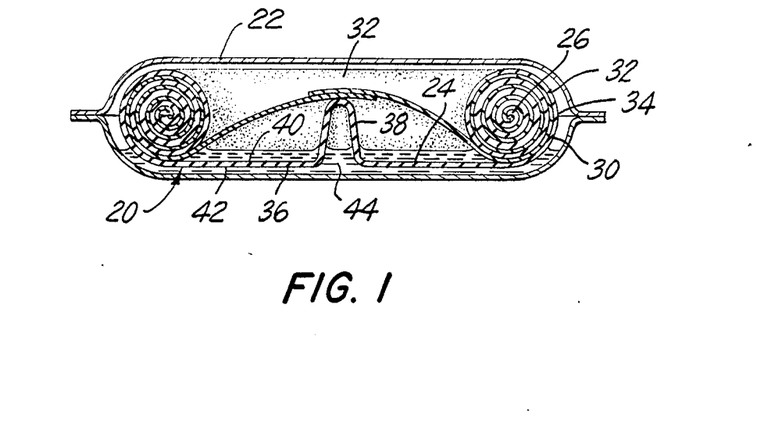
FIG. 1 is a cross-sectional view of a packaged condom constructed in accordance with the present invention.
Figure 2:
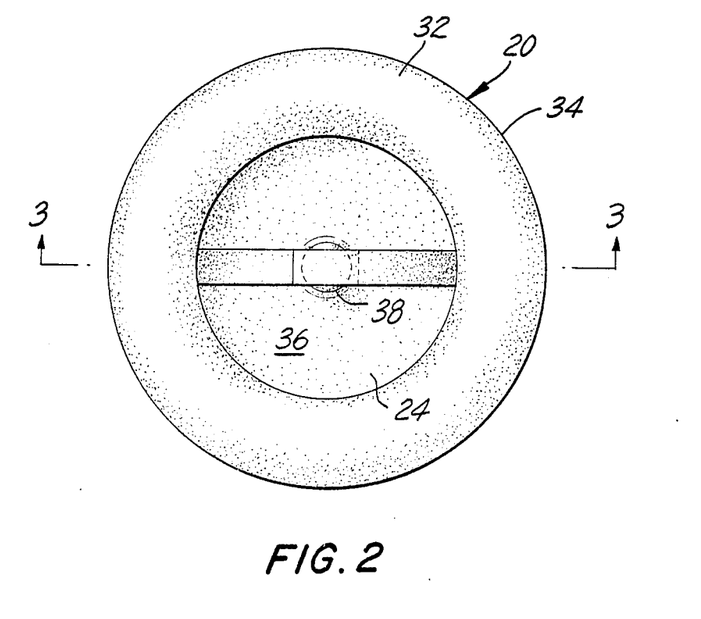
FIG. 2 is a top plan view of the condom.

Referring now to the drawing, and especially to FIG. 1 thereof, a protective sheath constructed in accordance with the invention is illustrated in the form of a condom 20 shown packaged within an envelope 22. Condom 20 has a first end 24 and a second end 26 and includes a tubular wall 30 of relatively thin, flexible material. In this instance, the material is an elastomer in the form of latex rubber; however, other materials commonly employed in the construction of condoms are available for use in connection with condom 20, an important characteristic of the material being the ability to roll up the tubular wall 30 into a relatively flattened configuration, as shown, for convenience of packaging. Thus, a portion 32 of tubular wall 30 is shown rolled up upon itself and lying along the perimeter 34 of the rolled up configuration of condom 20. A web 36 spans the first end 24 of the condom 20 and closes the first end 24. A well 38 is provided at the web 36 for enhancing the function of the condom 20. Tubular wall 30 includes an outer surface 40 and an inner surface 42, either one or both of which may be coated with, or otherwise exposed to, compounds providing a lubricant, a spermicide, or a bactericide as illustrated by the compounds 44 contained within the envelope 22.

Figure 3:
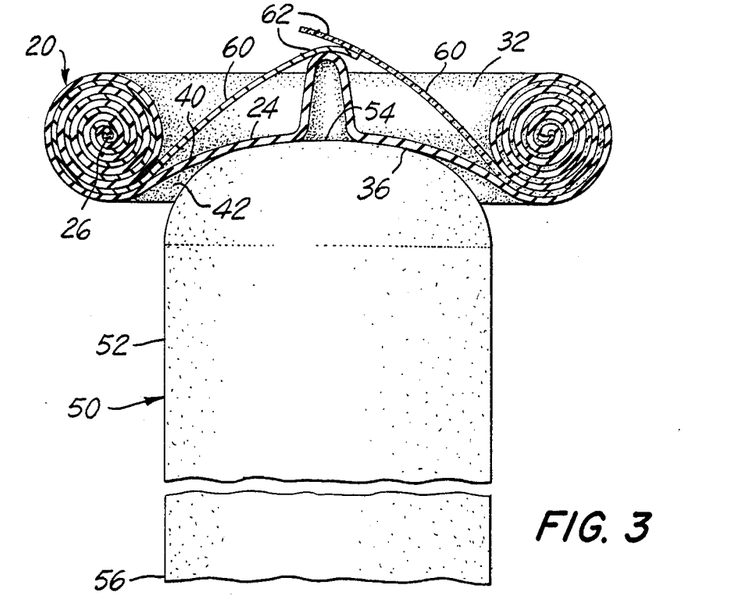
FIG. 3 is an enlarged cross-sectional view of the condom, taken along line 3—3 of FIG. 2, with the condom placed for application to a member.
Figure 4:
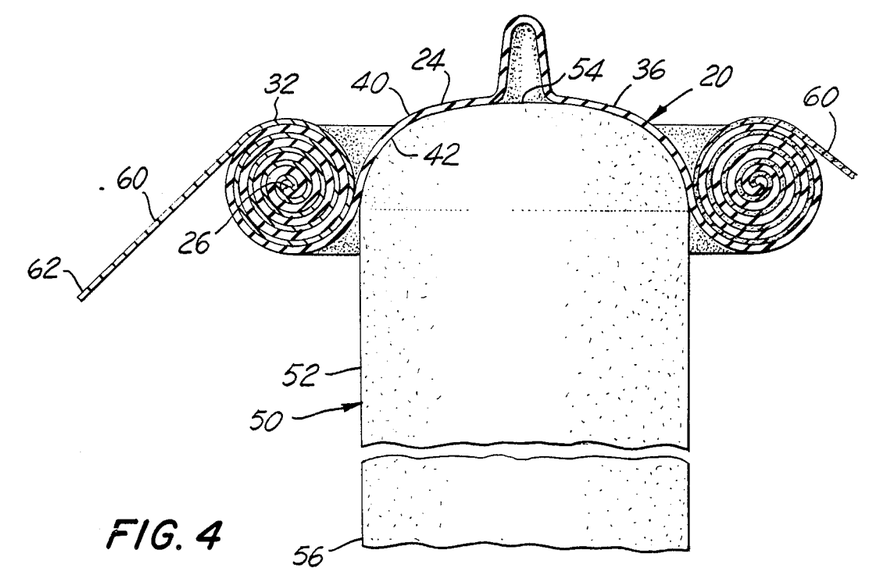
FIG. 4 is a view similar to FIG. 3, with the condom partially applied to the member.
Figures 5, 6:
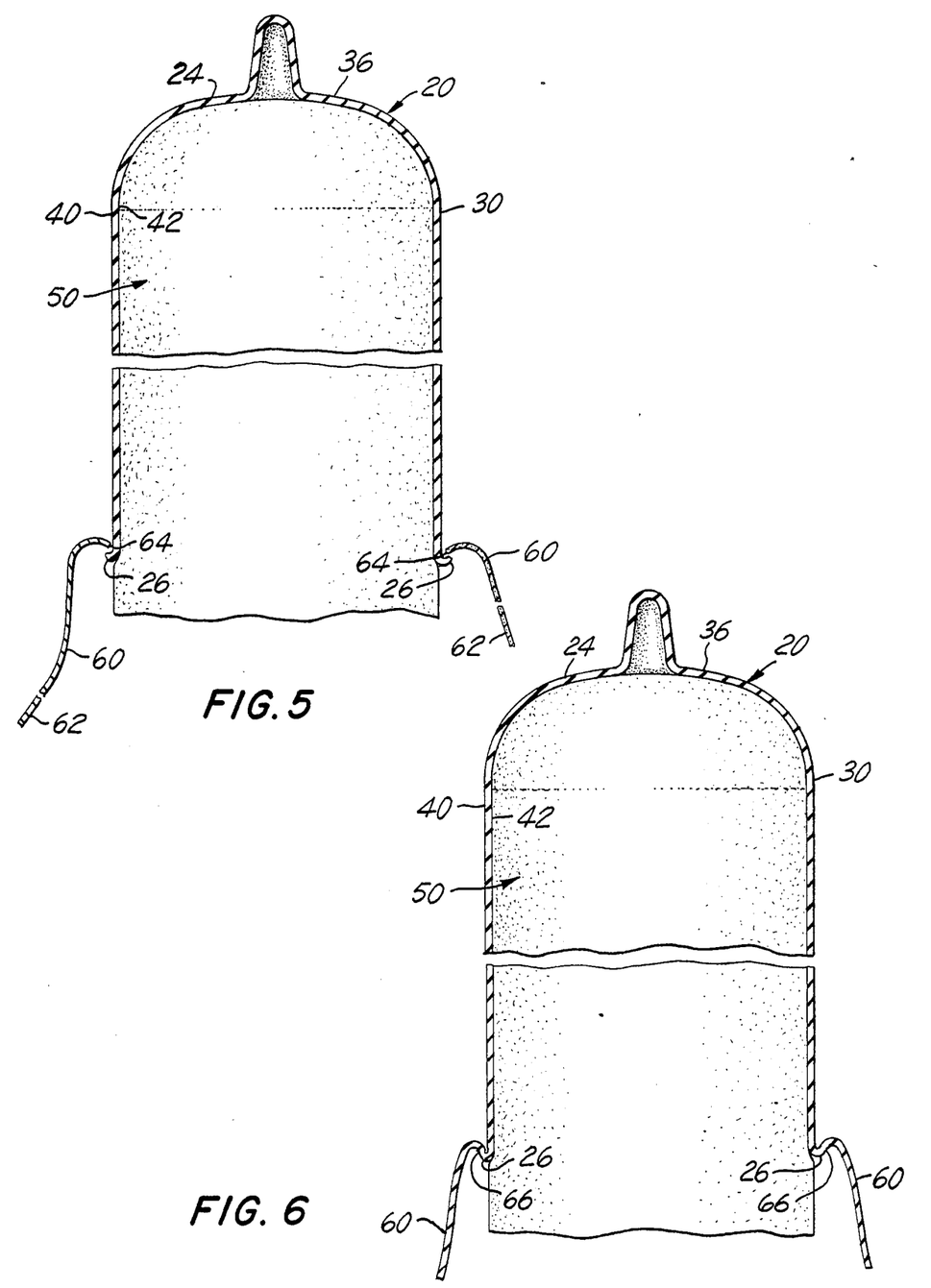
FIG. 5 is a view similar to FIG. 3, with the condom fully applied to the member.
FIG. 6 is a view similar to FIG. 5, but illustrating an alternative construction.

Turning now to FIGS. 2 through 5, the condom 20 is removed from the envelope 22 for application to a member 50 representing a male organ and having a generally cylindrical external surface 52 extending axially between opposite ends 54 and 56. In order to facilitate application of the condom 20 to the member 50, the present invention provides an improvement illustrated in the form of a pair of application tabs 60 interleaved with the rolled up tubular wall portion 32 and juxtaposed with the outer surface 40 of the tubular wall 30, the tabs 60 preferably being located essentially diametrically opposite one another. Each tab 60 extends along the outer surface 40, in the direction from the first end 24 toward the second end 26, preferably essentially all the way to the second end 26, and includes an application gripping portion in the form of a finger grip 62 adjacent the first end 24 of the tubular wall 30. Application of the condom 20 is accomplished by first locating the condom 20, in the rolled up state of the tubular wall 30, as illustrated in FIG. 3, at the end 54 of the member 50, with the inner surface 42 placed against the end 54 of the member 50. Placement of the condom 20 in the appropriate orientation is facilitated by the presence of the tabs 60 which provide both a visual and a tactile indication of the relative positions of the outer and inner surfaces 40 and 42. Once the condom 20 is so located, the finger grips 62 are grasped and the tabs 60 are pulled away from the one end 54, preferably toward the opposite end 56 of the member 50, as seen in FIG. 4, to unroll the rolled up tubular wall portion 32 and apply the condom 20 to the member 50, without the necessity for directly touching the tubular wall 30 of the condom 20. Continued pulling upon the tabs 60 will complete the application of the condom 20, as illustrated in FIG. 5. The remote end 64 of each tab 60 is free so that upon completion of the application of the condom 20 to the member 50, the application tabs 60 are pulled free of the tubular wall 30, and the condom 20, and may be discarded. The condom 20 then operates as a conventional condom.

Tabs 60 may be constructed of a material similar to that of tubular wall 30, or from any compatible material capable of being interleaved and rolled up with the rollable material of tubular wall portion 32. Finger grips 62 project away from the rolled up tubular wall portion 32 a distance sufficient to enable the grasping necessary to accomplish unrolling of the tubular wall portion 32 from the rolled up state of tubular wall 30, as illustrated in FIG. 3, to the unrolled state of tubular wall 30, as shown in FIG. 5. Since the condom 20 is applied without the necessity for touching the tubular wall 30, any compound 44 on the tubular wall 30 remains undisturbed. Likewise, the fingers of the user tend to remain free of any compound 44.

In the embodiment of FIG. 6, the applicator tabs 60 are integral with the tubular wall 30 at the corresponding remote ends 66 of the tabs 60 and the second end 26 of the condom 20 and may even be constructed unitary with the condom 20. While the construction of FIG. 6 is simple and enables simplified manufacturing techniques, it is not always desirable to have the tabs 60 remain integral with the condom 20 during use of the condom 20. Accordingly, as desired, the condom 20 may be provided with tabs 60 having free remote ends 64, as illustrated in the embodiment of FIGS. 2 through 5, or with affixed remote ends 66, as shown in FIG. 6. Another alternative would be to affix the remote ends 66 of the tabs 60 to the corresponding second end 26 of the condom 20, as with a perforated connection (not shown), so that tabs 60 may be removed selectively from the tubular wall 30 upon completion of the application of the condom 20.

Figure 7:
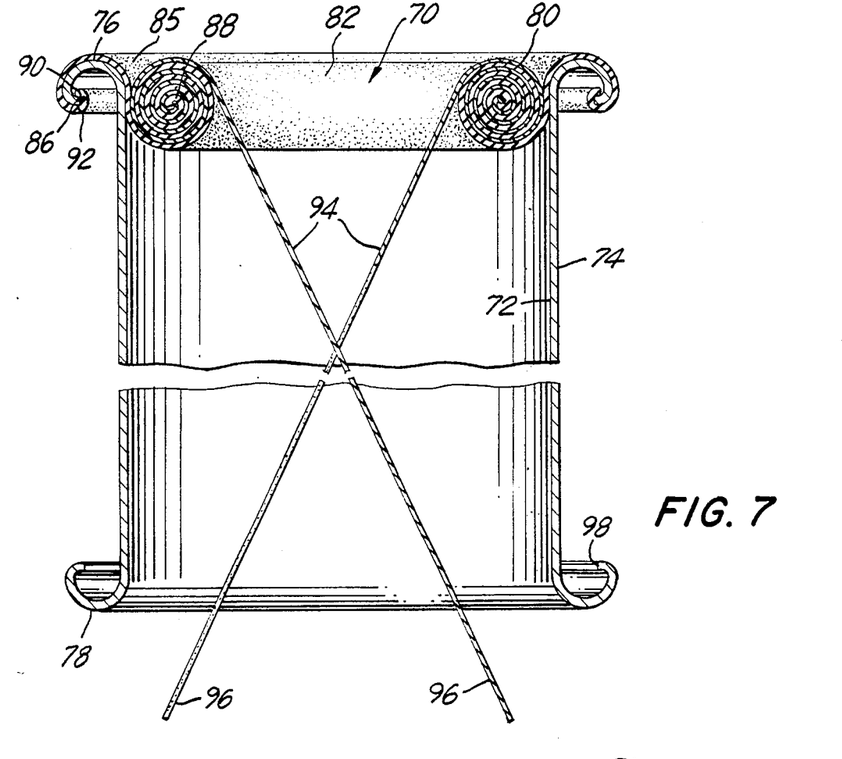
FIG. 7 is an elevational view, partially cross-sectioned, showing a liner constructed in accordance with the invention and about to be applied to the inner surface of a tubular member.
Figure 8:
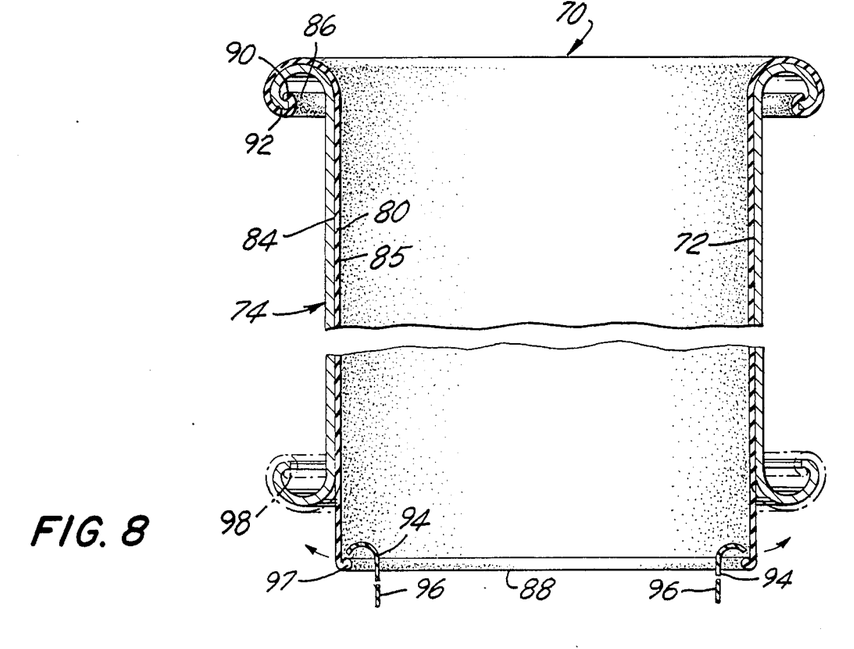
FIG. 8 is a view similar to FIG. 7 with the liner applied to the tubular member.

Referring now to FIGS. 7 and 8, another protective sheath is illustrated in the form of a liner 70 which embodies the improvement of the invention. Liner 70 is a thin, disposable element which is to be applied to the inner surface 72 of a hollow cylindrical member in the form of a tube 74 for the purpose of protecting either the inner surface 72 from the effects of a fluid to be passed through the tube 74, or for protecting the fluid from contact with the inner surface 72. For example, a corrosive fluid which otherwise could have a deleterious effect on the material of tube 74, when passed through the liner 70 in tube 74 will not corrode the liner 70 of elastomeric material, and the tube 74 will be preserved. Likewise, a septic fluid will not contaminate the inner surface 72 of tube 74 if passed through a disposable liner 70. Nor will a sterile fluid passed through the liner 70 in tube 74 be contaminated by contact with the inner surface 72 of the tube 74.

Tube 74 has opposite ends 76 and 78, both of which are open. Liner 70 has a tubular wall 80 constructed of a relatively thin material capable of being rolled up upon itself along at least a portion 82 of the tubular wall 80 into a relatively flattened configuration, as illustrated in FIG. 7. Tubular wall 80 has an outer surface 84 and an inner surface 85, both extending axially along the tubular wall 80 from a first end 86 to a second end 88. Each end 86 and 88 of the tubular wall 80 is open. Preferably, securing means is provided at the first end 86 of the tubular wall 80 for securing the first end 86 adjacent the end 76 of the tube 74. In the illustrated embodiment, the securing means is shown in the form of an elasticized ring 90 integral with the liner 70. The ring 90 grips the tube 74 beneath a rim 92 of the tube 74 and anchors the first end 86 of the tubular wall 80 of liner 70 against movement into the tube 74.

As in the earlier-described embodiments, a pair of essentially diametrically opposite application tabs 94 are interleaved with the rolled up tubular wall portion 82, juxtaposed with the outer surface 84 of the tubular wall 80, and include finger grips 96 projecting beyond the rolled up tubular wall portion 82 for grasping so as to pull the tabs 94 in the direction away from the first end 86 of the tubular wall 80 and toward the second end 88. The tabs 94 are long enough to reach beyond the opposite end 78 of the tube 74 so that the finger grips 96 are available for pulling from the opposite end 78 to unroll the tubular wall portion 82 and thereby apply the liner 70 to the inner surface 72 of the tube 74, as seen in FIG. 8. Once the liner 70 is in place within the tube 74, the tabs 94 may be released from the second end 88 of the tubular wall 80. If desired, a second elasticized ring 97 is provided at the second end 88 of the tubular wall 80 and may be anchored behind a second rim 98, located at the opposite end 78 of the tube 74, to secure the second end 88 in place, as illustrated in phantom in FIG. 8.

Turning now to FIGS. 9 through 12, another protective sheath constructed in accordance with the invention is illustrated in the form of a condom 100. As described in connection with the embodiment of FIGS. 1 through 5, condom 100 is to be applied to a member 110 representing a male organ and having a generally cylindrical external surface 112 extending axially between opposite ends 114 and 116. In order to facilitate application of the condom 100 to the member 110, application tabs 120 are interleaved with rolled up tubular wall portion 122 of tubular wall 124 and juxtaposed with the outer surface 126 of the tubular wall 124, the tabs 120 preferably being located essentially diametrically opposite one another. Each tab 120 extends along the outer surface 126, in the direction from the first end 128 of the condom 100 toward the second end 130, preferably essentially all the way to the second end 130, and includes an application gripping portion in the form of a finger grip 132 adjacent the first end 128 of the tubular wall 124.

Figures 9, 9A:
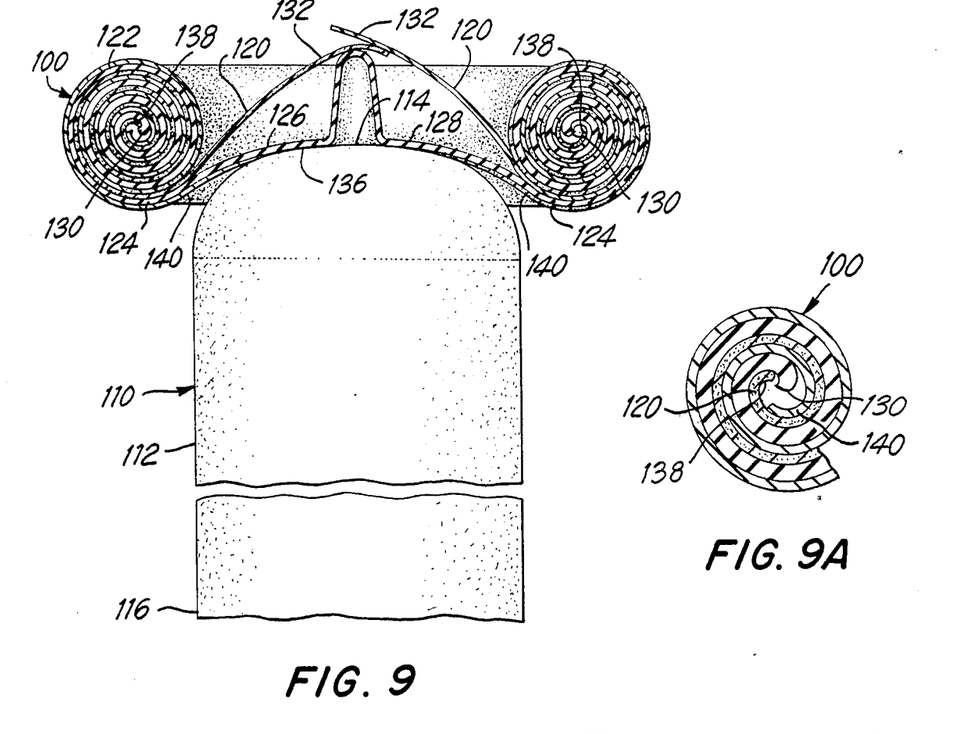
FIG. 9 is a cross-sectional view of another condom constructed in accordance with the invention and about to be applied to a member.
FIG. 9A is an enlarged fragmentary view of a portion of FIG. 9.
Figure 10:
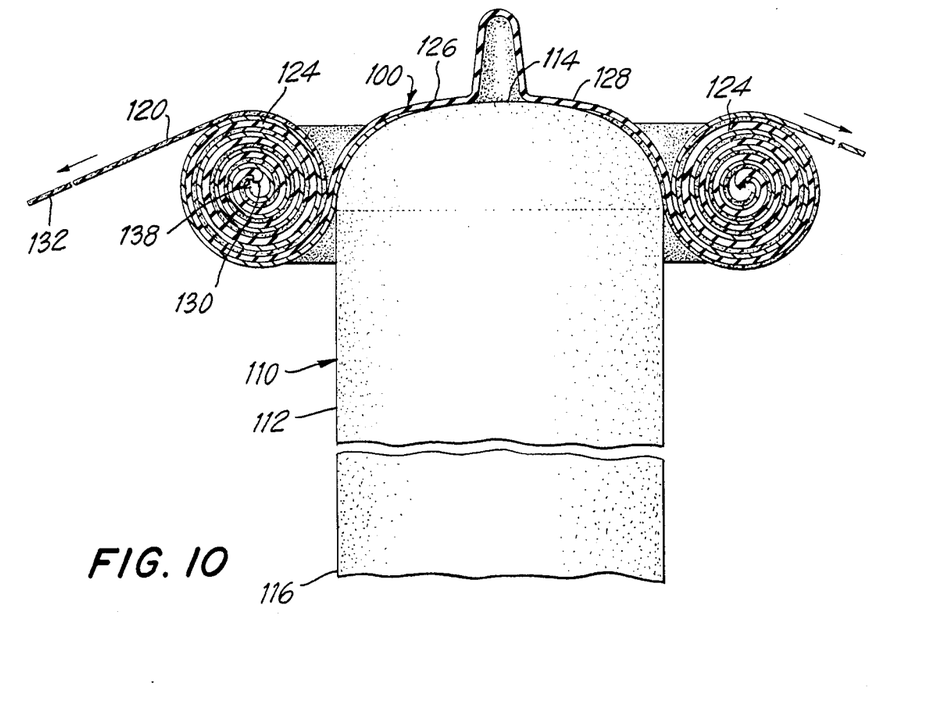
FIG. 10 is a view similar to FIG. 9, with the condom partially applied to the member.
Figures 11, 12:
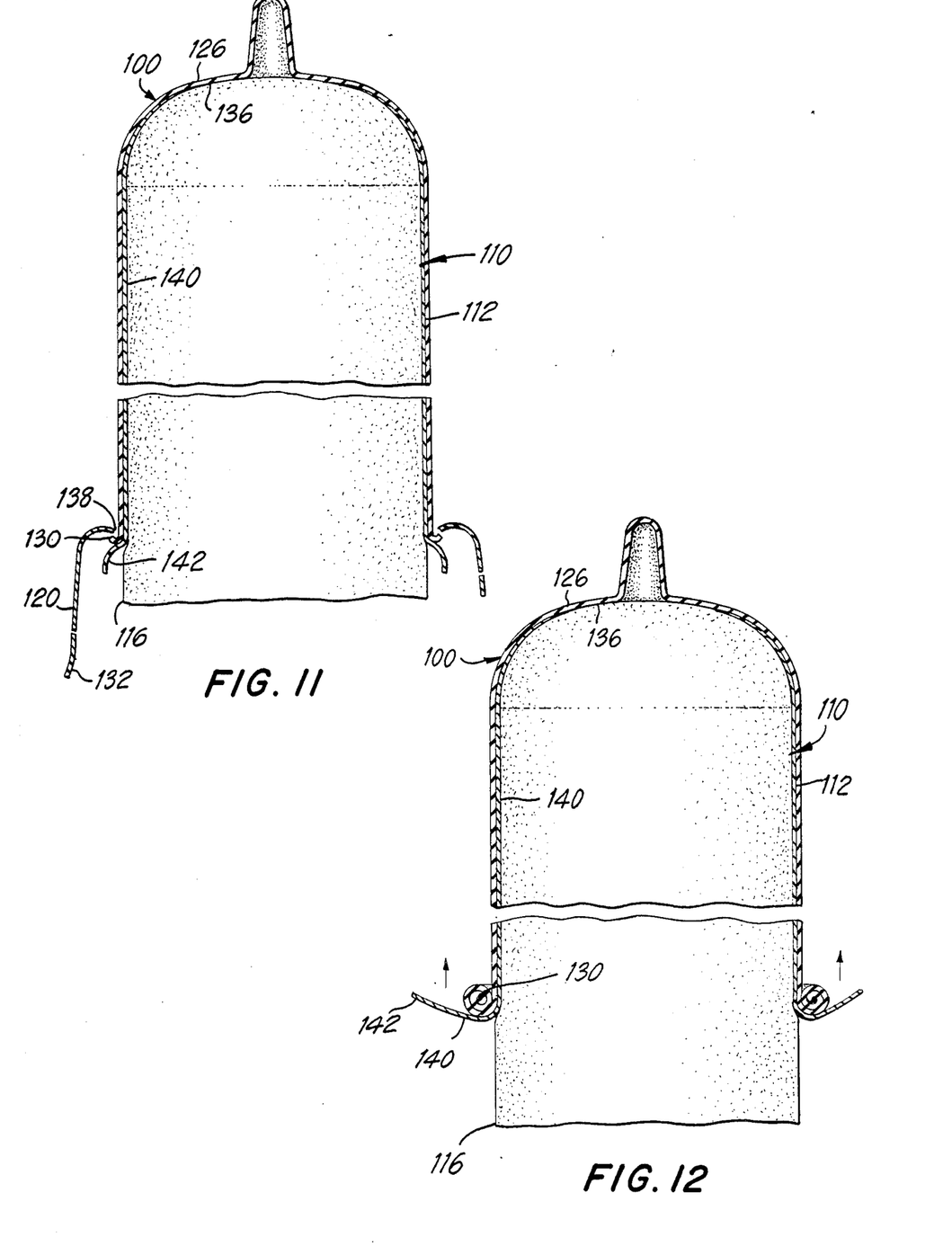
FIG. 11 is a view similar to FIG. 9, with the condom fully applied to the member.
FIG. 12 is a view similar to FIG. 9, showing the condom being removed.

Application of the condom 100 is accomplished by first locating the condom 100, in the rolled up state of the tubular wall 124, as illustrated in FIG. 9, at the end 114 of the member 110, with the inner surface 136 placed against the end 114 of the member 110. Placement of the condom 100 in the appropriate orientation is facilitated by the presence of the tabs 120 which provide both a visual and a tactile indication of the relative positions of the outer and inner surfaces 126 and 136. Once the condom 100 is so located, the finger grips 132 are grasped and the tabs 120 are pulled away from the one end 114, preferably toward the opposite end 116 of the member 100, as seen in FIG. 10, in a direction which will unroll the rolled up tubular wall portion 122 and apply the condom 100 to the member 110 without the necessity for directly touching the tubular wall 124 of the condom 100. Continued pulling upon the tabs 120 will complete the application of the condom 100, as illustrated in FIG. 11. The remote end 138 of each tab 120 is free so that upon completion of the application of the condom 100 to the member 110, the application tabs 120 are pulled free of the tubular wall 124, and thus free of the condom 100, and may be discarded. The condom 100 then operates as a conventional condom.

In order to facilitate removal of the condom 100 from the member 110, a pair of essentially diametrically opposite removal tabs 140 are juxtaposed with the inner surface 134 of the tubular wall portion 122 of the condom 100. Each removal tab 140 includes a removal gripping portion shown in the form of removal finger grips 142 which extend beyond the second end 130 of the condom 100 when the condom is applied to the member 110 so as to be available for gripping subsequent to the application of the condom 100. Upon gripping of the finger grips 142 and pulling outwardly, as shown, the tubular wall portion 122 will be rolled up along the outer surface 112 of the member 110, as illustrated in FIG. 12, and then off the member 110, for removal of the condom 100 from the member 110, without direct contact between the fingers of the user and the tubular wall 124. In this manner aseptic conditions and cleanliness are maintained.

The removal tabs 140 are very thin and preferably are constructed of the same or similar material as is employed for the tubular wall 124 of the condom 100. Accordingly, the removal tabs 140 do not interfere with the application and use of the condom 100. When the tubular wall 124 is in the rolled up state, and the tubular wall portion 122 is rolled up upon itself, the removal tabs 140 are interleaved with the tubular wall portion 122 and are unobtrusive.

Figures 13, 13A:
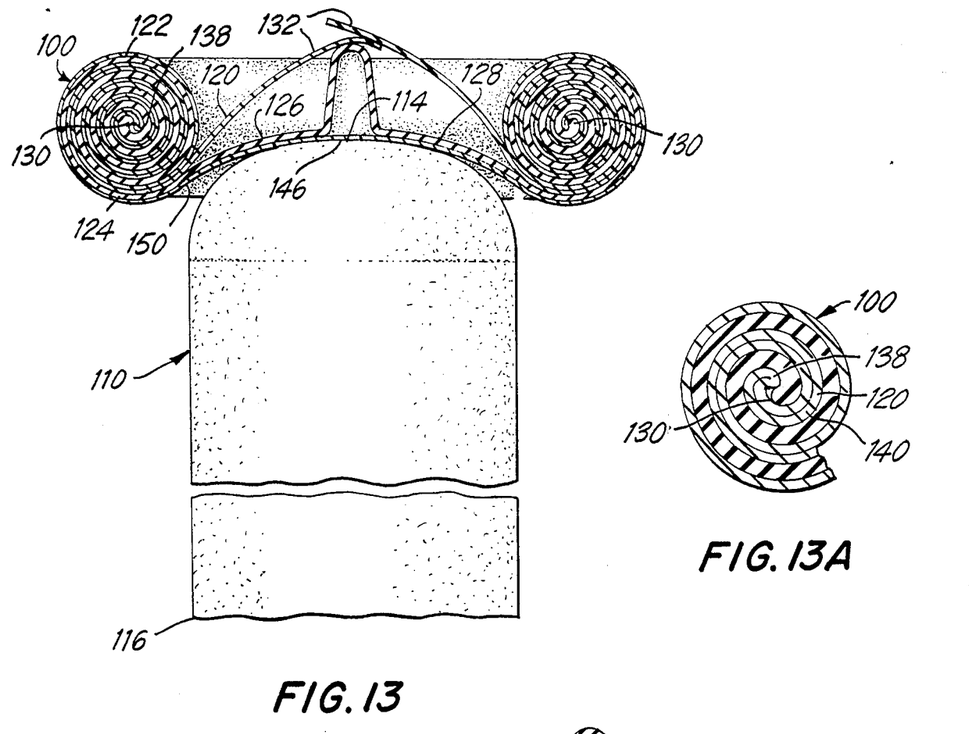
FIG. 13 is a view similar to FIG. 9, showing another condom constructed in accordance with the invention.
FIG. 13A is an enlarged fragmentary view of a portion of FIG. 13.
Figure 14:
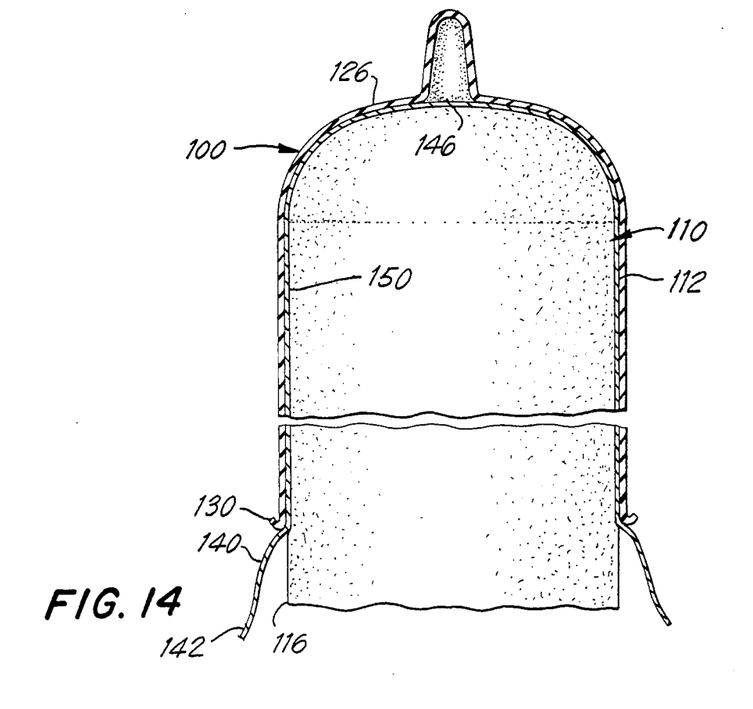
FIG. 14 is a view similar to FIG. 13, with the condom fully applied.

The embodiment of FIGS. 13 through 14 is similar to that described above in connection with FIGS. 9 through 12, and the same reference characters are employed to refer to similar component parts. However, in the present embodiment, each application tab 120 is unitary with a corresponding removal tab 140 at the remote end 138 of the application tab 120 for simplified manufacture. In order to further simplify construction, the removal tabs 140 are joined together at the remote ends 144 thereof by means of a bridging member 146. In this manner, the application tabs 120 and the removal tabs 140 all are a part of one unitary strip 150, rendering the construction simple and easy to manufacture.

While the above-described embodiments of the invention are described as having a pair of diametrically opposite application tabs and a pair of diametrically opposite removal tabs, it will be apparent that the number and location of these tabs may be varied without affecting the basic function of the tabs. The described pairs of tabs are illustrative of preferred embodiments.

It will be apparent that the present invention provides an improvement which attains the several objects and advantages set forth above; namely, simplifies application by facilitating the initial orientation and location of the rolled up protective sheath upon the corresponding member and then unrolling of the protective sheath for application to the member; avoids direct handling of the protective sheath itself during application, and in some embodiments during removal, so as to maintain aseptic conditions, as well as general cleanliness, while facilitating the manipulations required for application and removal; provides an ergonomic construction enabling ease of use with minimal instruction; permits increased ease of use of the protective sheath without disturbing the function of the protective sheath, and with no deleterious effects upon the disposable nature of the protective sheath; and provides a simplified construction which is economical to manufacture in large quantities of uniform high quality.

It is to be understood that the above detailed description of preferred embodiments of the invention is provided by way of example only. Various details of design and construction may be modified without departing from the true spirit and scope of the invention as set forth in the appended claims.

The embodiments of the invention in which an exclusive property or privilege is claimed are defined as follows:

1. An improvement in a protective sheath adapted for application to a generally cylindrical member, along a generally complementary cylindrical surface of the cylindrical member, the cylindrical surface having axially opposite ends, the protective sheath having first and second ends and a tubular wall of relatively thin, rollable flexible material, the tubular wall including an outer surface and an inner surface and capable of being rolled and unrolled between a rolled up state, wherein at least a portion of the tubular wall is rolled up upon itself in a relatively flattened configuration, and an unrolled state, wherein the tubular wall portion extends axially in a tubular configuration, the protective sheath being adapted for application along the generally complementary cylindrical surface by juxtaposing the tubular wall, in the rolled up state, with one of the opposite ends of the cylindrical surface and then unrolling the rolled up tubular wall portion to extend the tubular wall from the rolled up state toward the unrolled state along the cylindrical surface, the improvement comprising:

at least one application tab interleaved with the rolled up portion of the tubular wall, when the tubular wall is in the rolled up sate, and juxtaposed with the outer surface of the tubular wall such that the application tab extends along the outer surface of the tubular wall from the first end of the protective sheath toward the second end thereof, the application tab including an application gripping portion extending beyond the rolled up tubular wall portion adjacent the first end of the protective sheath so as to be available for gripping and pulling away from the first end of the protective sheath to unroll the rolled up tubular wall portion toward the unrolled state of the tubular wall for application of the protective sheath along the cylindrical surface; and at least one removal tab interleaved with the rolled up portion of the tubular wall, when the tubular wall is in the rolled up state, and juxtaposed with the inner surface of the tubular wall such that the removal tab extends along the inner surface of the tubular wall from the second end of the protective sheath toward the first end thereof, when the tubular wall is in the unrolled state, the removal tab including a removal gripping portion extending beyond the second end of the protective sheath so as to be available for gripping and pulling away from the second end of the protective sheath to roll the tubular wall portion from the unrolled state of the tubular wall toward the rolled up state and effect removal of the protective sheath from the cylindrical surface;

the application tab and the removal tab being integral with one another.

2. An improvement in a protective sheath adapted for application to a generally hollow cylindrical member, along a generally complementary cylindrical inner surface of the cylindrical member, the cylindrical inner surface having axially opposite open ends, the protective sheath having a first end, an open second end and a tubular wall of relatively thin, rollable flexible material, the tubular wall including an outer surface and an inner surface and capable of being rolled and unrolled between a rolled up state, wherein at least a portion of the tubular wall is rolled up upon itself in a relatively flattened configuration, and an unrolled state, wherein the tubular wall portion extends axially in a tubular configuration, the protective sheath being adapted for application along the generally complementary inner cylindrical surface by juxtaposing the tubular wall, in the rolled up state, with one of the opposite ends of the cylindrical inner surface and then unrolling the rolled up tubular wall portion to extend the tubular wall from the rolled up state toward the unrolled state along the cylindrical inner surface, the improvement comprising:

at least one application tab interleaved with the rolled up portion of the tubular wall, when the tubular wall is in the rolled up state, and juxtaposed with the outer surface of the tubular wall such that the application tab extends along the outer surface of the tubular wall from the first end of the protective sheath toward the second end thereof, the application tab including an application gripping portion extending beyond the rolled up tubular wall portion adjacent the first end of the protective sheath so as to be available for gripping and pulling away from the first end of the protective sheath to unroll the rolled up tubular wall portion toward the unrolled state of the tubular wall for application of the protective sheath along the cylindrical inner surface of the hollow cylindrical member; and securing means adjacent the first end of the protective sheath for securing the first end of the protective sheath at one of the opposite ends of the cylindrical inner surface of the hollow cylindrical member, while the tubular wall portion is unrolled from the rolled up state of the tubular wall toward the unrolled state.

3. The improvement of claim 2 including at least two of said application tabs, the application tabs being located essentially diametrically opposite one another, the application tabs each including an application gripping portion extending toward the opposite application gripping portion.

4. An improvement in a protective sheath for application to a generally cylindrical member, along a generally complementary cylindrical outer surface of the cylindrical member, the outer cylindrical surface having axially opposite ends, the protective sheath having first and second ends and a tubular wall of relatively thin, rollable flexible material, the tubular wall including an outer surface and an inner surface and capable of being rolled and unrolled between a rolled up state, wherein at least a portion of the tubular wall is rolled up upon itself in a relatively flattened configuration, and an unrolled state, wherein the tubular wall portion extends axially in a tubular configuration, the protective sheath being adapted for application along the generally complementary cylindrical outer surface by juxtaposing the tubular wall, in the rolled up state, with one of the opposite ends of the cylindrical outer surface and then unrolling the rolled up tubular wall portion to extend the tubular wall from the rolled up state toward the unrolled state along the cylindrical outer surface, the improvement comprising:

at least two application tabs located diametrically opposite one another and interleaved with the rolled up portion of the tubular wall, when the tubular wall is in the rolled up state, and juxtaposed with the outer surface of the tubular wall such that the application tabs extend along the outer surface of the tubular wall from the first end of the protective sheath toward the second end thereof, the application tabs each including an application gripping portion extending toward the opposite application gripping portion adjacent the first end of the protective sheath so as to be available for gripping and pulling away from the first end of the protective sheath to unroll the rolled up tubular wall portion toward the unrolled state of the tubular wall for application of the protective sheath along the cylindrical outer surface; and at least two removal tabs located essentially diametrically opposite one another and interleaved with the rolled up portion of the tubular wall, when the tubular wall is in the rolled up state, and juxtaposed with the inner surface of the tubular wall such that the removal tabs extend along the inner surface of the tubular wall from the second end of the protective sheath toward the first end thereof, when the tubular wall is in the unrolled state, the removal tabs each including a removal gripping portion extending toward the opposite removal gripping portion so as to be available for gripping and pulling away from the second end of the protective sheath to roll the tubular wall portion from the unrolled state of the tubular wall toward the rolled up state and effect removal of the protective sheath from the cylindrical outer surface; and a web at the first end of the protective sheath, the web extending diametrically across the first end of the sheath to close the first end of the sheath and abut the cylindrical member at the one of the opposite ends of the cylindrical outer surface of the cylindrical member corresponding to the first end of the protective sheath, the removal gripping portions each extending adjacent the web of the protective sheath.

5. The improvement of claim 4 including a bridging portion extending along the web and joining together the two removal tabs.

6. The improvement of claim 4 wherein each application tab is unitary with a corresponding removal tab.

7. In a condom of the type having a closed first end, an open second end and a tubular wall of relatively thin, rollable flexible material, the tubular wall including an outer surface and an inner surface and capable of being rolled and unrolled between a rolled up state, wherein at least a portion of the tubular wall is rolled up upon itself in a relatively flattened configuration, and an unrolled state, wherein the tubular wall portion extends axially in a tubular configuration, for application of the condom along a generally complementary cylindrical surface having axially opposite ends by juxtaposing the tubular wall, in the rolled up state, with one of the opposite ends of the cylindrical surface and then unrolling the rolled up tubular wall portion from the rolled up state of the tubular wall toward the unrolled state along the cylindrical surface, the improvement comprising:

at least one application tab interleaved with the rolled up tubular wall portion when the tubular wall is in the rolled up state, the application tab including an application gripping portion extending beyond the rolled up tubular wall portion adjacent the first end of the condom so as to be available for gripping and pulling away from the first end of the condom to unroll the rolled up tubular wall portion toward the unrolled state of the tubular wall and apply the condom along the cylindrical state; and at least one removal tab interleaved with the rolled up portion of the tubular wall, when the tubular wall is in the rolled up state, and juxtaposed with the inner surface of the tubular wall such that the removal tab extends along the inner surface of the tubular wall from the second end of the condom toward the first end thereof, when the tubular wall is in the unrolled state, the removal tab including a removal gripping portion extending beyond the second end of the condom so as to be available for gripping and pulling away from the second end of the condom to roll the tubular wall portion from the unrolled state of the tubular wall toward the rolled up state and effect removal of the condom from the cylindrical surface;

the application tab and the removal tab being integral with one another.

8. In a condom of the type having a closed first end, an open second end and a tubular wall of relatively thin, rollable flexible material, the tubular wall including an outer surface and an inner surface and capable of being rolled and unrolled between a rolled up state, wherein at least a portion of the tubular wall is rolled up upon itself in a relatively flattened configuration, and an unrolled state, wherein the tubular wall portion extends axially in a tubular configuration, for application of the condom along a generally complementary cylindrical surface having axially opposite ends by juxtaposing the tubular wall, in the rolled up state, with one of the opposite ends of the cylindrical surface and then unrolling the rolled up tubular wall portion from the rolled up state of the tubular wall toward the unrolled state along the cylindrical surface, the improvement comprising:

at least two application tabs located essentially diametrically opposite one another and interleaved with the rolled up tubular wall portion when the tubular wall is in the rolled up state, the application tabs each including an application gripping portion extending toward the opposite application gripping portion, adjacent the closed first end of the condom, so as to be available for gripping and pulling away from the first end of the condom to unroll the rolled up tubular wall portion toward the unrolled state of the tubular wall for application of the condom along the cylindrical surface; and at least two removal tabs located essentially diametrically opposite one another and interleaved with the rolled up portion of the tubular wall, when the tubular wall is in the rolled up state, and juxtaposed with the inner surface of the tubular wall such that the removal tabs extend along the inner surface of the tubular wall from the second end of the condom toward the first end thereof, when the tubular wall is in the unrolled state, the removal tabs each including a removal gripping portion extending beyond the second end of the condom so as to be available for gripping and pulling away from the second end of the condom to roll the tubular wall portion from the unrolled state of the tubular wall toward the rolled up state for removal of the condom from the cylindrical surface.

9. The improvement of claim 8 including a bridging portion extending along the closed end and joining together the two removal tabs.

10. The improvement of claim 8 wherein each application tab is unitary with a corresponding removal tab.

* * * * *